United States Patent
Kang et al.

(10) Patent No.: US 12,084,408 B2
(45) Date of Patent: *Sep. 10, 2024

(54) METHOD FOR DECOMPOSING PHENOL-BASED BY-PRODUCT

(71) Applicant: LG CHEM, LTD., Seoul (KR)

(72) Inventors: Min Suk Kang, Daejeon (KR); Sang Beom Lee, Daejeon (KR); Chi Hyun Jang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 383 days.

This patent is subject to a terminal disclaimer.

(21) Appl. No.: 17/619,211

(22) PCT Filed: May 31, 2021

(86) PCT No.: PCT/KR2021/006714
§ 371 (c)(1),
(2) Date: Dec. 14, 2021

(87) PCT Pub. No.: WO2022/010102
PCT Pub. Date: Jan. 13, 2022

(65) Prior Publication Data
US 2022/0281791 A1    Sep. 8, 2022

(30) Foreign Application Priority Data
Jul. 10, 2020  (KR) ........................ 10-2020-0085515

(51) Int. Cl.
| | | |
|---|---|---|
| C07C 37/74 | (2006.01) | |
| C07C 1/20 | (2006.01) | |
| C07C 7/04 | (2006.01) | |
| C07C 37/52 | (2006.01) | |
| C07C 37/56 | (2006.01) | |
| C07C 37/72 | (2006.01) | |
| C07C 45/82 | (2006.01) | |

(52) U.S. Cl.
CPC ............... *C07C 37/74* (2013.01); *C07C 1/20* (2013.01); *C07C 7/04* (2013.01); *C07C 37/52* (2013.01); *C07C 37/56* (2013.01); *C07C 37/72* (2013.01); *C07C 45/82* (2013.01)

(58) Field of Classification Search
CPC .. C07C 37/74; C07C 1/20; C07C 7/04; C07C 37/52; C07C 45/82
See application file for complete search history.

(56) References Cited

U.S. PATENT DOCUMENTS

| | | | |
|---|---|---|---|
| 4,158,611 A | 6/1979 | Cooke | |
| 4,246,203 A | 1/1981 | Wirth | |
| 5,510,543 A | 4/1996 | Fulmer et al. | |
| 11,247,958 B2* | 2/2022 | Kang | ................ B01D 3/4266 |
| 11,370,735 B2* | 6/2022 | Lee | ........................ C07C 1/20 |

FOREIGN PATENT DOCUMENTS

| | | |
|---|---|---|
| CN | 102992961 A | 3/2013 |
| CN | 110785393 A | 2/2020 |
| JP | 2005-029478 A | 2/2005 |
| KR | 10-0396718 B1 | 12/2003 |
| KR | 10-2019-0057697 A | 5/2019 |
| KR | 10-2019-0058273 A | 5/2019 |
| KR | 10-2020-0077027 A | 6/2020 |
| KR | 10-2020-0077248 A | 6/2020 |

* cited by examiner

*Primary Examiner* — Sikarl A Witherspoon
(74) *Attorney, Agent, or Firm* — Bryan Cave Leighton Paisner LLP

(57) ABSTRACT

Provided is a method of decomposing phenol-based by-product, and more particularly, a method of decomposing phenol-based by-product including: introducing a phenol-based by-product stream, a first stream of a side discharge stream from a decomposition device, and a process water stream to a mixing device and mixing the streams; introducing a discharge stream from the mixing device to a layer separation device to phase-separate the discharge stream into an oil phase and an aqueous phase; passing an oil stream discharged from the layer separation device through any one or more of a first heat exchanger and a second heat exchanger and introducing the oil stream to the decomposition device to carry out decomposition; and supplying the first stream of the side discharge stream from the decomposition device to the mixing device, forming a mixed stream of a second stream of the side discharge stream with a lower discharge stream and discharging the mixed stream, and recovering effective components from an upper discharge stream.

11 Claims, 2 Drawing Sheets

[FIG. 1]
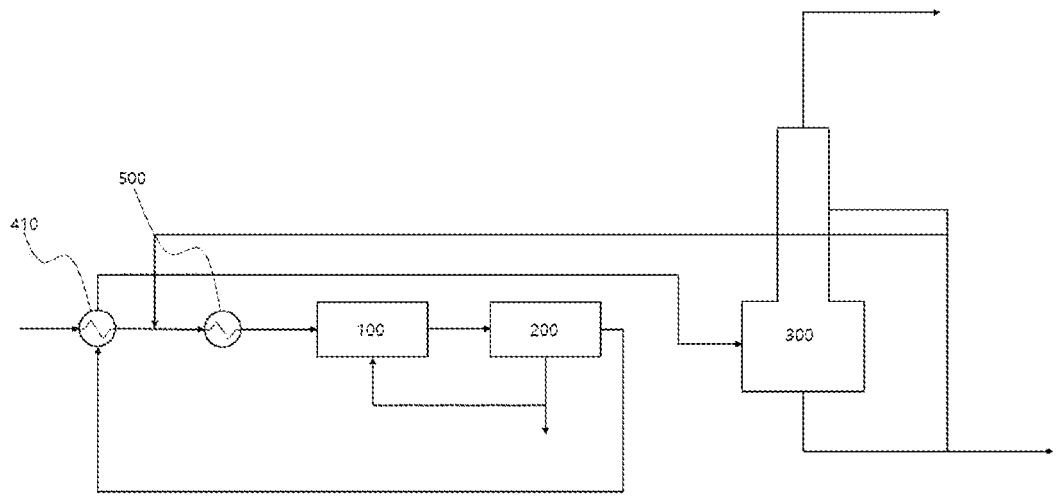
[FIG. 2]
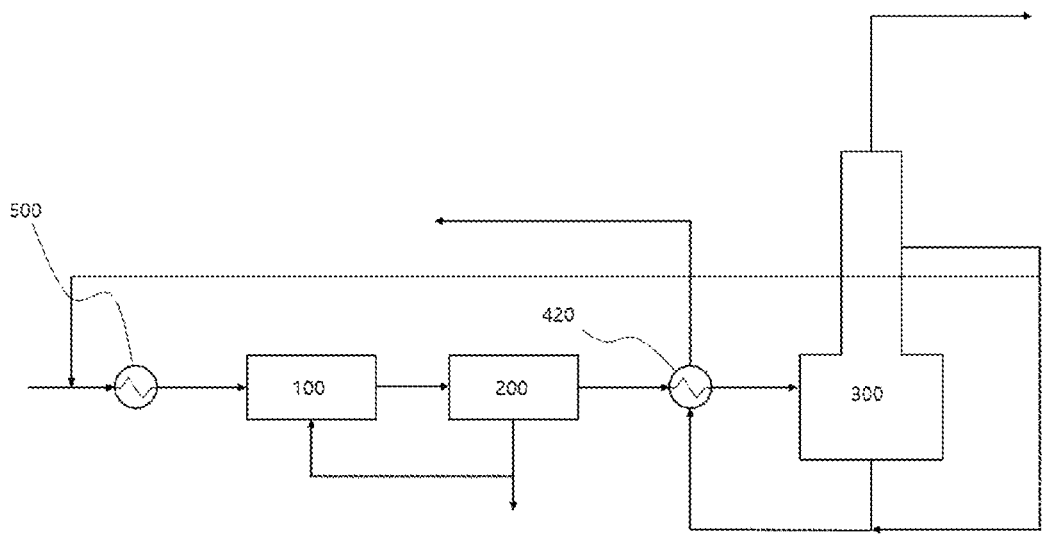

【FIG. 3】
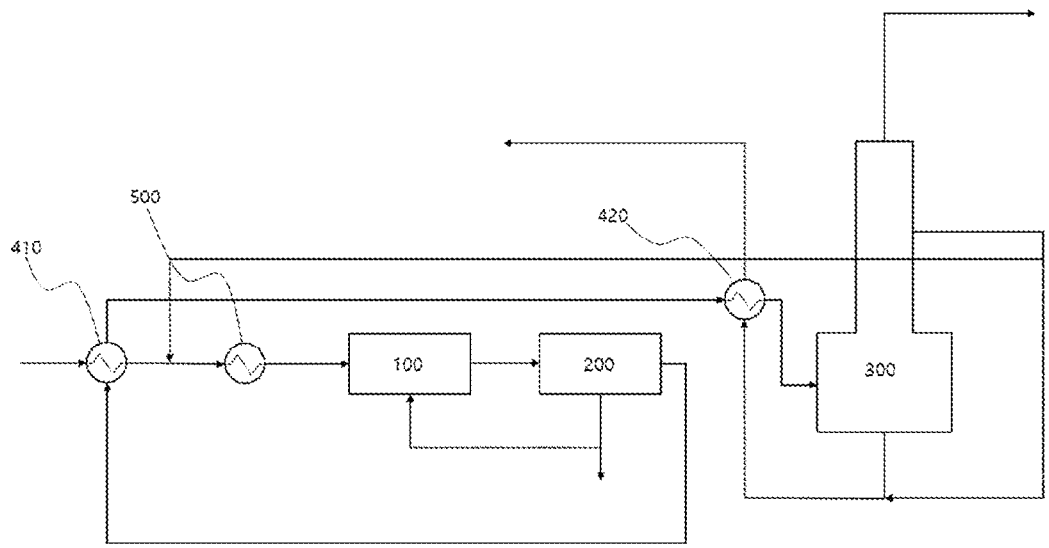
【FIG. 4】
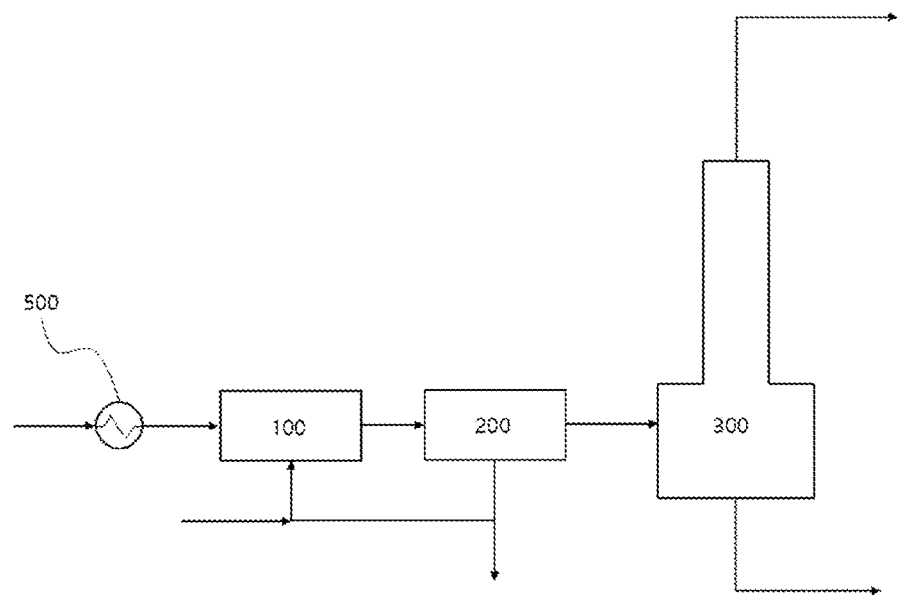

METHOD FOR DECOMPOSING PHENOL-BASED BY-PRODUCT

CROSS-REFERENCE TO RELATED APPLICATIONS

The present application is a National Phase entry pursuant to 35 U.S.C. § 371 of International Application No. PCT/KR2021/006714, filed on May 31, 2021, and claims the benefit of and priority to Korean Patent Application No. 10-2020-0085515, filed on Jul. 10, 2020, the entire contents of which are incorporated by reference in their entirety for all purposes as if fully set forth herein.

TECHNICAL FIELD

The present invention relates to a method of decomposing phenol-based by-product, and more particularly, to a method of decomposing phenol-based by-product, which can effectively separate effective components from phenol-based by-product and also, can reduce an amount of energy used.

BACKGROUND ART

About 95% of phenols used around the world are generally produced by a Hock process. The Hock process is carried out by three steps of: (1) alkylating benzene by propylene to form cumene, (2) binding the cumene with oxygen to oxidize cumene to cumene hydroperoxide (CHP), and (3) decomposing cumene hydroperoxide into phenol and acetone by an acid decomposition reaction in the presence of an acid catalyst.

Here, in step (2) of oxidizing cumene, by-product such as acetophenone (AP), dimethyl benzyl alcohol (DMBA), dicumyl peroxide (DCP), and dicumene (DC) are produced, in addition to cumene hydroperoxide.

In addition, in step (3) of acid decomposition reaction of cumene hydroperoxide, hydroxy acetone (HA), 2-methylbenzofuran (2-MBF), α-methylstyrene (AMS), mesityl oxide (MO), an α-methylstyrene dimer (AMS dimer), cumylphenol (CP), and the like are produced as by-product, in addition to phenol and acetone.

Therefore, since a product stream produced by the reaction process described above is present in a state in which phenol, acetone, and various by-products are mixed, a series of separation processes for separating phenol from the product stream is required.

The product stream is introduced to a separate separation device, in which an acetone-based mixture including unreacted cumene, acetone, α-methylstyrene, hydroxyacetone, and the like is separated in the tower top of the separation device and a phenol-based mixture including phenol, a part of α-methylstyrene and 2-methylbenzofuran, other by-products, and the like is separated in the tower bottom of the separation device.

The phenol-based mixture separated from the tower bottom of the separation device is introduced to a phenol column, in which phenol is separated in the tower top of the phenol column and phenol-based by-product such as dicumyl peroxide, cumylphenol, α-methylstyrene dimer, and tar are separated in the tower bottom of the phenol column.

In addition, in general, a process of producing bisphenol A (BPA) is a process of condensing phenol and acetone produced from the Hock process in the presence of an acidic catalyst or a cation exchange resin to produce bisphenol A.

Thus, unreacted phenol, unreacted acetone, trisphenol (BPX), tar, and the like are produced as by-products, in addition to bisphenol A, in the bisphenol A reaction product stream.

From the by-products produced in the phenol process and the bisphenol A preparation process, effective components such as phenol, cumene, and α-methylstyrene can be recovered by a separate decomposition device, and a study of the decomposition process and the decomposition device allowing efficient recovery of the effective components is in progress.

DISCLOSURE

Technical Problem

An object of the present invention is to provide a method which decomposes phenol-based by-product to obtain effective components and uses a side discharge stream from a decomposition device to reuse heat from the side discharge stream from the decomposition device in the process, thereby reducing energy.

Technical Solution

In one general aspect, a method of decomposing phenol-based by-product includes: introducing a phenol-based by-product stream, a first stream of a side discharge stream from a decomposition device, and a process water stream to a mixing device and mixing the streams; introducing a discharge stream from the mixing device to a layer separation device to phase-separate the stream into an oil phase and an aqueous phase; passing an oil stream discharged from the layer separation device through any one or more of a first heat exchanger and a second heat exchanger and introducing the stream to the decomposition device to carry out decomposition; and supplying the first stream of the side discharge stream from the decomposition device to the mixing device, forming a mixed stream of a second stream of the side discharge stream with a lower discharge stream and discharging the mixed stream, and recovering effective components from an upper discharge stream.

Advantageous Effects

According to the method of decomposing phenol-based by-product according to the present invention, when the phenol-based by-product are decomposed to obtain effective components, high value-added effective components from which salts are removed can be obtained, and also a side discharge stream from a decomposition device is utilized to reuse heat of the side discharge stream from the decomposition device, thereby reducing energy.

DESCRIPTION OF DRAWINGS

FIGS. 1 to 3 are process flow diagrams for a method of decomposing phenol-based by-product according to an exemplary embodiment of the present invention, respectively.

FIG. 4 is a process flow diagram for a method of decomposing phenol-based by-product according to the comparative example.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

In the present invention, the term "stream" may refer to a fluid flow in a process, or may refer to a fluid itself flowing in a pipe. Specifically, the "stream" may refer to both a fluid itself flowing in a pipe connecting each device and a fluid flow. In addition, the fluid may refer to a gas or a liquid.

Hereinafter, the present invention will be described in more detail with reference to the FIGS. 1 to 3 for better understanding of the present invention.

According to the present invention, a method of decomposing phenol-based by-product is provided. The method of decomposing phenol-based by-product can include: introducing a phenol-based by-product stream, a first stream of a side discharge stream from a decomposition device 300, and a process water stream to a mixing device 100 and mixing the streams; introducing a discharge stream from the mixing device 100 to a layer separation device 200 to phase-separate the stream into an oil phase and an aqueous phase; passing an oil stream discharged from the layer separation device 200 through any one or more of a first heat exchanger 410 and a second heat exchanger 420 and introducing the stream to the decomposition device 300 to carry out decomposition; and supplying the first stream of the side discharge stream from the decomposition device 300 to the mixing device 100, forming a mixed stream of a second stream of the side discharge stream with a lower discharge stream and discharging the mixed stream, and recovering effective components from an upper discharge stream.

According to an exemplary embodiment of the present invention, the phenol-based by-product can include any one or more of phenol-based by-product produced in a phenol preparation process and phenol-based by-product produced in a bisphenol A preparation process. For example, the phenol-based by-product can be phenol-based by-product produced in the phenol preparation process, phenol-based by-product produced in the bisphenol A preparation process, or a mixture of the phenol-based by-product produced in the phenol preparation process and the phenol-based by-product produced in the bisphenol A preparation process.

The phenol preparation process can be carried out by the Hock process described above. Specifically, the phenol preparation process can be carried out by a step of decomposing and purifying cumene hydroperoxide prepared by an oxidation reaction of cumene to separate phenol and acetone. The step of decomposing and purifying cumene hydroperoxide prepared by the oxidation reaction of cumene to separate phenol and acetone is a step of using a cumene purification process and a phenol/acetone purification process. First, propylene and benzene are alkylated to prepare cumene and then heavy/light by-products are discharged by a purification process and cumene is purified and separated. Subsequently, the purified cumene is oxidized to prepare cumene hydroperoxide (CHP), the cumene hydroperoxide (CHP) is decomposed under a common acid catalyst such as sulfuric acid ($H_2SO_4$) to produce phenol, acetone, α-methylstyrene (AMS), and heavy by-products, and through a purification process, α-methylstyrene (AMS) and heavy by-products are discharged and phenol and acetone are purified and separated.

Since a product stream produced by the reaction process described above is present in a state in which phenol, acetone, and various by-products are mixed, a series of separation processes for separating phenol from the product stream is required.

The product stream is introduced to a separate separation device, in which an acetone-based mixture including unreacted cumene, acetone, α-methylstyrene, hydroxyacetone, and the like is separated in the tower top of the separation device and a phenol-based mixture including phenol, a part of α-methylstyrene and 2-methylbenzofuran, other by-products, and the like is separated in the tower bottom of the separation device.

The phenol-based mixture separated from the tower bottom of the separation device is introduced to a phenol column, in which phenol is separated in the tower top of the phenol column and phenol-based by-product such as dicumyl peroxide, cumylphenol, alpha-methylstyrene dimer, and tar are separated in the tower bottom of the phenol column. As a result, the phenol-based by-product produced from the phenol preparation process can include some effective components such as phenol, cumene, and α-methylstyrene, and tar.

In addition, the bisphenol A preparation process can be carried out by a method of reacting phenol and acetone prepared by the Hock process described above to prepare bisphenol A, and recovering bisphenol A from the reaction product. Specifically, the bisphenol A preparation process can be carried out by: decomposing and purifying cumene hydroperoxide prepared by an oxidation reaction of cumene to separate phenol and acetone; separating bisphenol A prepared by reacting the separated phenol and acetone and decomposing a stream including unseparated bisphenol A under an aqueous alkaline solution; and separating the reaction product by the decomposition reaction, phenol-based by-product, and acetone-based by-products.

The step of decomposing and purifying cumene hydroperoxide prepared by the oxidation reaction of cumene to separate phenol and acetone is a step of using a cumene purification process and a phenol/acetone purification process. First, propylene and benzene are alkylated to prepare cumene and then heavy/light by-products are discharged by a purification process and cumene is purified and separated. Subsequently, the purified cumene is oxidized to prepare cumene hydroperoxide (CHP), the cumene hydroperoxide (CHP) is decomposed under a common acid catalyst such as sulfuric acid ($H_2SO_4$) to produce phenol, acetone, α-methylstyrene (AMS), and heavy by-products, and through a purification process, α-methylstyrene (AMS) and heavy by-products are discharged and phenol and acetone are purified and separated.

The step of separating bisphenol A prepared by reacting the separated phenol and acetone and decomposing a stream including unseparated bisphenol A under an aqueous alkaline solution is a step of using a bisphenol A (BPA) purification process. First, the purified and separated phenol and acetone are reacted to prepare bisphenol A, more correctly crude bisphenol A, and then a crystallization process was carried out to prepare bisphenol A having an improved purity. Bisphenol A prepared as such is separated by a BPA purification process and by-products including unseparated bisphenol A are decomposed under an excessive amount of the aqueous alkaline solution having properties of a base such as NaOH, KOH, and LiOH.

In the step of separating the reaction product by the decomposition reaction, phenol-based by-product, and acetone-based by-products, the stream after the decomposition reaction can be supplied to a separation device to separate an acetone-based mixture in a tower top of the separation device and separate a reaction product in a tower bottom of the separation device. The reaction product is introduced to a bisphenol A/phenol column where bisphenol A is separated in the tower top, and phenol-based by-product such as bisphenol A, phenol, dicumyl peroxide, cumylphenol, an α-methylstyrene dimer, and tar are separated in the tower bottom. Here, the phenol-based by-product include bisphenol A which is a product, and effective components such as cumene and α-methylstyrene, in addition to tar which is an impurity.

As a result, the phenol-based by-product produced from the bisphenol A preparation process can include some effective components such as phenol, cumene, and α-methylstyrene, and tar, with bisphenol A.

Therefore, a mixture of the phenol-based by-product produced in the bisphenol A preparation process and phenol-based by-product produced in the phenol preparation process can include one or more selected from the group consisting of bisphenol A, phenol, α-methylstyrene, acetophenone, cumylphenol, and an α-methylstyrene dimer. As a specific example, the phenol-based by-product can include two or more selected from the group consisting of bisphenol A, phenol, α-methylstyrene, acetophenone, cumylphenol, and an α-methylstyrene dimer, or all of them.

The phenol-based by-product can include the phenol-based by-product produced in the bisphenol A preparation process and the phenol-based by-product produced in the phenol preparation process at a flow rate ratio of 1:2 to 10. For example, the phenol-based by-product can include the phenol-based by-product produced in the bisphenol A preparation process and the phenol-based by-product produced in the phenol preparation process at a flow rate ratio of 1:2 to 10, 1:4 to 10, or 1:6 to 10. As such, it can be preferred to decompose phenol-based by-product having a high content of the phenol-based by-product produced in the phenol preparation process relative to the phenol-based by-product produced in the bisphenol A preparation process, in terms of preventing a load on the decomposition device 300 and reducing an amount of energy used in the process.

According to an exemplary embodiment of the present invention, the phenol preparation process and the bisphenol A preparation process can be carried out by including the acid decomposition reaction of cumene hydroperoxide described above. Here, since the acid decomposition reaction of cumene hydroperoxide is carried out by including an acid, an acid decomposition reaction solution includes an acid. Therefore, in order to obtain phenol and acetone by a process such as distillation from the acid decomposition reaction solution, a process of neutralizing the acid decomposition reaction solution is needed.

Thus, the acid decomposition reaction solution is neutralized by an aqueous basic solution before being separated, where in the neutralized acid decomposition reaction solution, salts from a reaction between an acid used in the acid decomposition reaction and a base such as an aqueous basic solution are produced. The acid decomposition reaction solution neutralized by a neutralization process is separated into an oil phase and an aqueous phase and a separation process for obtaining phenol and acetone from the separated oil phase is carried out, and most of the salts are removed with the aqueous phase, but some salts remain in the oil phase.

The salts remain in the phenol-based by-product described in the present invention. The salts remaining in the phenol-based by-product as such causes corrosion, occlusion, and deposition of the decomposition device 300 during the decomposition of the phenol-based by-product for obtaining effective components from the phenol-based by-product, thereby resulting in device failure. Therefore, during the decomposition of the phenol-based by-product, it is important to minimize salts in the phenol-based by-product.

Thus, as a method for removing salts in the phenol-based by-product, a process water is introduced before decomposing the phenol-based by-product, to remove the salts, can be considered, but in this case, phase separation of the oil phase and the aqueous phase is not carried out well, and thus, the salts may not be sufficiently removed.

In addition, a method of introducing an organic material such as cumene and α-methylstyrene discharged as an effective component from an acetone column and the like in the phenol preparation process together with the process water to the phenol-based by-product, thereby removing salts, can be considered, but in this case, since cumene and α-methylstyrene should be obtained as a product again, an overload occurs in the phenol preparation process and the entire operation energy is increased.

In addition, a method of introducing an organic material such as an upper discharge stream of the decomposition device 300 including effective components for decomposing the phenol-based by-product to the phenol-based by-product with the process water, thereby removing salts, can be considered, but since the method uses the upper discharge stream of the decomposition device 300 obtained as effective components as it is, purification efficiency is decreased and the stream to be refluxed is decreased, so that cooling/heating for operating a condenser is further needed in the upper portion of the decomposition device 300, resulting in an increase in overall operation energy.

However, according to the method of decomposing phenol-based by-product according to the present invention, it is possible to minimize salts in the phenol-based by-product, and thus, it is possible to stably operate the phenol-based by-product decomposition device 300, and the phenol-based by-product can be decomposed to effectively obtain effective components.

Specifically, in the present invention, as a method of removing salts in the phenol-based by-product, before decomposing the phenol-based by-product, the phenol-based by-product stream is supplied to a mixing device 100, and the side discharge stream from the decomposition device 300 and a process water stream are introduced separately to the mixing device 100, thereby minimizing salts remaining the phenol-based by-product. Here, as the side discharge stream from the decomposition device 300 supplied to the mixing device 100, a first stream which is a part of the side discharge stream of the decomposition device 300 can be supplied.

The phenol-based by-product can include one or more selected from the group consisting of bisphenol A, phenol, α-methylstyrene, acetophenone, cumylphenol, and an α-methylstyrene dimer, as described above. As a specific example, the phenol-based by-product can include two or more selected from the group consisting of bisphenol A, phenol, α-methylstyrene, acetophenone, cumylphenol, and an α-methylstyrene dimer, or all of them.

The process water is for dissolving salts in the phenol-based by-product stream therein and removing the salts, and can mean including all various aqueous solutions such as an acidic aqueous solution and a basic aqueous solution, in addition to distilled water.

The process water can have a pH of 3.5 to 7, 3.5 to 5.5, or 3.5 to 4.5, and within the range, corrosion of the mixing device 100 and the layer separation device 200 is prevented, solubility of the salts is improved, and phase separation ability in separation of an oil phase and an aqueous phase in the layer separation device 200 can be improved.

The mixing device 100 can be a mixer for mixing the phenol-based by-product and the process water. As a specific example, the mixer can be provided with a line mixer or a static mixer for easily carrying out mixing of the phenol-based by-product and the process water.

The side discharge stream from the decomposition device 300 is a stream discharged from the side of the decomposition device 300 described later, and can include one or more selected from the group consisting of phenol, acetophenone, isopropylphenol, α-methylstyrene, and cumene. As a specific example, the side discharge stream from the decomposition device 300 can include phenol, acetophenone, isopropylphenol, α-methylstyrene, and cumene. The reason why the side discharge stream from the decomposition device 300 is introduced to the mixing device 100 is that acetophenone included in the side discharge stream from the decomposition device 300 activates phase separation of an oil phase and an aqueous phase including salts in the phase separation using the layer separation device 200 described later, thereby minimizing salts remaining in the oil phase.

According to an exemplary embodiment of the present invention, the phenol-based by-product are a stream supplied from any one process of the phenol preparation process and the bisphenol A preparation process, and a supplied temperature can be high, for example, in a range of 200° C. or higher, 200° C. to 300° C., or 200° C. to 250° C. Therefore, in order to prevent vaporization of the process water before supplying the phenol-based by-product stream to the mixing device 100, the phenol-based by-product stream can be cooled. Specifically, the phenol-based by-product stream can be cooled using a separate cooler 500 and then supplied to the layer separation device 200. In addition, the phenol-based by-product stream can be cooled by being passed through a first heat exchanger 410, before being cooled in the cooler 500. Specifically, the phenol-based by-product stream can be cooled by heat exchange with the oil stream discharged from the layer separation device 200 described later in the first heat exchanger 410, and then, can be further cooled in the cooler 500. As such, energy for cooling the phenol-based by-product stream can be reduced by the heat exchange with the stream in the process, and simultaneously, the oil stream discharged from the layer separation device 200 can be heated before being supplied to the decomposition device 300, thereby reducing energy used in the decomposition device 300.

The phenol-based by-product stream can be introduced to the mixing device 100 with the first stream of the side discharge stream from the decomposition device 300 and the process water stream and be mixed therewith. For example, the phenol-based by-product stream and the first stream of the side discharge stream from the decomposition device 300 can be mixed before being cooled in the cooler 500 and be cooled by the cooler 500, and after being cooled, can be introduced to the mixing device 100 and be mixed with the process water introduced to the mixing device 100.

The phenol-based by-product stream, the first stream of the side discharge stream from the decomposition device 300, and the process water stream, which are introduced to the mixing device 100, can be 1:0.2 to 0.8:1 to 3, 1:0.3 to 0.7:1.2 to 2.8, or 1:0.4 to 0.6:1.3 to 1.8. By controlling the flow rate ratio of the phenol-based by-product stream, the first stream of the side discharge stream from the decomposition device 300, and the process water stream to the above range, not only the mixing of the phenol-based by-product stream, the first stream of the side discharge stream from the decomposition device 300, and the process water stream but also the phase separation ability of the oil phase and the aqueous phase in the layer separation device 200 described later is improved, and removal efficiency of salts included in the phenol-based by-product is improved.

According to an exemplary embodiment of the present invention, a discharge stream from the mixing device 100 which is discharged from the mixing device 100 is supplied to the layer separation device 200, and can be phase-separated into the oil phase and the aqueous phase in the layer separation device 200. Specifically, in the layer separation device 200, the discharge stream from the mixing device 100 can be phase-separated into the oil phase and the aqueous phase, for removing salts included in the discharge stream from the mixing device 100 and introducing the stream to the decomposition device 300.

The oil stream discharged from the layer separation device 200 is a stream obtained by removing salts from the phenol-based by-product stream and can be used as a supply stream to the decomposition device 300, and the oil stream discharged from the layer separation device 200 is in a state of having a minimized content of salts, and thus, can prevent corrosion, occlusion, deposition, and the like of the decomposition device 300 in the decomposition reaction of the decomposition device 300.

The aqueous stream discharged from the layer separation device 200 can include salts remaining in the phenol-based by-product and the process water. Accordingly, salts can be removed from the phenol-based by-product stream.

A part of the stream of the aqueous stream discharged from the layer separation device 200 can be supplied to the mixing device 100 and be reused. In addition, of the aqueous stream discharged from the layer separation device 200, the remaining stream which has not been supplied to the mixing device 100 can be discharged as waste water including salts.

The layer separation device 200 can be a drum for phase-separating the oil phase and the aqueous phase.

For phase-separating the oil phase and the aqueous phase from the layer separation device 200, a step of retaining the discharge stream from the mixing device 100 in the layer separation device 200 for 1 hour to 10 hours, 2 hours to 8 hours, or 3 hours to 5 hours, can be included. As such, when the stream discharged from the mixing device 100 is retained in the layer separation device 200, phase separation can occur more clearly, and thus, salts can be removed as much as possible from the phenol-based by-product.

The oil stream discharged from the layer separation device 200 can be supplied to the decomposition device 300 for a decomposition reaction. Here, the oil stream discharged from the layer separation device 200 can be heated using the stream in the process before being supplied to the decomposition device 300, while being passed through any one or more of the first heat exchanger 410 and the second heat exchanger 420. For example, the oil stream discharged from the layer separation device 200 can be heated using the phenol-based by-product stream while being passed through the first heat exchanger 410, heated using a mixed stream of the second stream of the side discharge stream from the decomposition device 300 described later and the lower discharge stream while being passed through the second heat exchanger 420, or heated secondly while being passed through both the first heat exchanger 410 and the second heat exchanger 420. As a result, the oil stream discharged from the layer separation device 200 can be supplied to the decomposition device 300 after being heated using the stream in the process while being passed through any one or more of the first heat exchanger 410 and the second heat exchanger 420.

According to an exemplary embodiment of the present invention, decomposition carried out in the decomposition device 300 can be thermal decomposition, and the decomposition device 300 for carrying out this can be a thermal cracker. As a specific example, the thermal cracker can be a reactor-distillation tower integrated separation device.

The effective components are separated from the upper portion of the decomposition device 300, and for effectively separating a heavy material including tar from the lower portion, the decomposition device 300 can be operated at a temperature of 260° C. to 370° C., 290° C. to 370° C., or 300° C. to 350° C. and a pressure of 0.1 bar to 3 bar, 0.1 bar to 2 bar, or 0.1 bar to 1.0 bar.

In the decomposition device 300, the effective components can be separated from the upper discharge stream. The effective components can include one or more selected from the group consisting of, for example, phenol, α-methylstyrene, and cumene. In addition, the lower discharge stream from the decomposition device 300 is a stream including tar, and can be recovered and reused as a fuel and the like.

The side discharge stream from the decomposition device 300 can be discharged at 25% to 90%, 40% to 90%, or 50% to 90% of the total number of stages of the decomposition device 300. In this case, acetophenone discharged to the upper discharge stream from the decomposition device 300 can be significantly reduced.

The side discharge stream from the decomposition device 300 can include 40 wt % or more of acetophenone. For example, the side discharge stream from the decomposition device 300 can include 40 wt % to 99 wt %, 55 wt % to 99 wt %, or 60 wt % to 99 wt % of acetophenone. The acetophenone is an organic material included in the phenol-based by-product stream, and since it acts as an impurity in contrast to the effective components obtained by the phenol-based by-product decomposition reaction, it is preferred to minimize the content of acetophenone in the effective components. Therefore, when according to the present invention, the side discharge stream from the decomposition device 300 includes wt % or more of acetophenone, the side discharge stream from the decomposition device 300 can be separated to minimize the content of acetophenone in the effective components obtained by the phenol-based by-product decomposition reaction, and thus, it is advantageous for obtaining the effective components.

The side discharge stream from the decomposition device 300 can branch to a first stream and a second stream. For example, the first stream of the side discharge stream from the decomposition device 300 is supplied to the mixing device 100 to improve salt removal efficiency in the phenol-based by-product stream and the second stream is passed through the second heat exchanger 420 and discharged, whereby pollutants accumulated in the second heat exchanger 420 can be dissolved and removed while the oil stream discharged from the layer separation device 200 is heated and the flowability of the lower discharge stream from the decomposition device 300 is improved.

Specifically, as described above, the first stream of the side discharge stream from the decomposition device 300 having a high content of acetophenone can be used to effectively remove salts included in the phenol-based by-product stream.

In addition, the second stream of the side discharge stream from the decomposition device 300 can be used to improve the flowability of the lower discharge stream from the decomposition device 300 having a high content of tar to have bad flowability. For example, the lower discharge stream from the decomposition device 300 is mixed with the second stream to form a mixed stream, and the mixed stream can be passed through the second heat exchanger 420 to be discharged. Thus, since the viscosity of the lower discharge stream from the decomposition device 300 can be lowered to improve flowability, and simultaneously, the organic material included in the side discharge stream from the decomposition device 300 has a composition, a temperature, and the like appropriate for dissolving pollutants accumulated in the heat exchanger, for example, a tar component, the pollutants accumulated in the inner wall, the pipe, and the like of the heat exchanger can be effectively dissolved within a short time to be removed.

In addition, since the decomposition device 300 is operated at a high temperature, the side discharge stream is also discharged at a high temperature, and the second stream of the side discharge stream from the decomposition device 300 at a high temperature is used as a heat source for heating the stream in the process, thereby reducing energy. For example, the temperature of the side discharge stream from the decomposition device 300 can be 150° C. to 400° C., 150° C. to 300° C., or 180° C. to 250° C. As such, the second stream of the side discharge stream from the decomposition device 300 at a high temperature is passed through the second heat exchanger 420 with the lower discharge stream from the decomposition device 300 and discharged, thereby improving the flowability of the lower discharge stream from the decomposition device 300 and also heating the oil stream of the layer separation device 200 which has been passed through the first heat exchanger 410 supplied to the second heat exchanger 420.

According to an exemplary embodiment of the present invention, in the method of decomposing phenol-based by-product, if necessary, devices such as a distillation column (not shown), a condenser (not shown), a reboiler (not shown), a valve (not shown), a pump (not shown), a separator (not shown), and a mixer (not shown) can be further installed.

Hereinabove, the method of decomposing phenol-based by-product according to the present invention has been described and illustrated in the drawings, but the description and the illustration in the drawings are the description and the illustration of only core constitutions for understanding of the present invention, and in addition to the process and apparatus described above and illustrated in the drawings, the process and the apparatus which are not described and illustrated separately can be appropriately applied and used for carrying out the method of decomposing phenol-based by-product according to the present invention.

Hereinafter, the present invention will be described in more detail by the Examples. However, the following Examples are provided for illustrating the present invention. It is apparent to a person skilled in the art that various modifications and alterations may be made without departing from the scope and spirit of the present invention, and the scope of the present invention is not limited thereto.

EXAMPLES

Example 1

Referring to the process flow diagram illustrated in FIG. 1, the process was simulated, using an Aspen Plus simulator from Aspen Technology, Inc. Specifically, a phenol-based by-product stream having the composition shown in the following Table 1 having a flow rate of 1,000 kg/hr was passed through a first heat exchanger 410 at a temperature of 211° C., mixed with a first stream of a side discharge stream from a decomposition device 300, supplied to a mixing device 100 in a state of being cooled to 80° C. by passing the stream through a cooler 500, and mixed with a process water stream at pH 4 in the mixing device 100. A flow ratio of the phenol-based by-product stream: the first stream of the side discharge stream from the decomposition device 300: the process water stream was controlled to 1:0.25:1.25, based on 1,000 kg/hr of the phenol-based by-product stream.

A discharge stream from the mixing device 100 was supplied to a layer separation device 200 and retained for 5 hours in the layer separation device 200, and an oil stream discharged therefrom was supplied to the decomposition device 300 operated at 0.1 KG in a state of being heated to 136° C. by passing the stream through the first heat exchanger 410.

Effective components were obtained from the upper discharge stream from the decomposition device 300, the first stream of the side discharge stream discharged at 200° C. was supplied to the mixing device 100, and the second stream was mixed with the lower discharge stream and discharged.

The compositions of the upper discharge stream and the side discharge stream from the decomposition device 300 are shown in the following Table 2.

TABLE 1

| Classification | | Phenol-based by-product stream |
|---|---|---|
| Phenol | (wt %) | 4.85 |
| α-methylstyrene | (wt %) | 7.14 |
| Acetophenone | (wt %) | 11.60 |
| Cumylphenol | (wt %) | 15.32 |
| α-methylstyrene dimer | (wt %) | 10.74 |
| Bisphenol A | (wt %) | 11.56 |
| Others | (wt %) | 38.79 |
| Total | (wt %) | 100.00 |

TABLE 2

| Classification | | Upper discharge stream from decomposition device | Side discharge stream from decomposition device |
|---|---|---|---|
| Phenol | (wt %) | 32.99 | 19.87 |
| α-methylstyrene | (wt %) | 50.07 | 5.92 |
| Cumene | (wt %) | 11.83 | 0.94 |
| Acetophenone | (wt %) | 0.01 | 46.75 |
| Isopropylphenol | (wt %) | 0.00 | 26.19 |
| Others | (wt %) | 5.10 | 0.33 |
| Total | (wt %) | 100.00 | 100.00 |

Example 2

Referring to the process flow diagram illustrated in FIG. 2, the process was simulated, using an Aspen Plus simulator from Aspen Technology, Inc. Specifically, a phenol-based by-product stream having the composition shown in Table 1 having a flow rate of 1,000 kg/hr was mixed with a first stream of a side discharge stream from a decomposition device 300 at a temperature of 211° C., supplied to a mixing device 100 in a state of being cooled to 80° C. by passing the stream through a cooler 500, and mixed with a process water stream at pH 4 in the mixing device 100. A flow ratio of the phenol-based by-product stream: the first stream of the side discharge stream from the decomposition device 300: the process water stream was controlled to 1:0.25:1.25, based on 1,000 kg/hr of the phenol-based by-product stream.

The discharge stream from the mixing device 100 was supplied to a layer separation device 200 and retained for 5 hours in the layer separation device 200, and an oil stream discharged therefrom was supplied to the decomposition device 300 operated at 0.1 KG in a state of being heated to 159° C. by passing the stream through the second heat exchanger 420.

Effective components were obtained from the upper discharge stream from the decomposition device 300, the first stream of the side discharge stream discharged at 200° C. was supplied to the mixing device 100, and the second stream was mixed with the lower discharge stream and passed through the second heat exchanger 420 to be discharged.

Example 3

Referring to the process flow diagram illustrated in FIG. 3, the process was simulated, using an Aspen Plus simulator from Aspen Technology, Inc. Specifically, a phenol-based by-product stream having the composition shown in Table 1 having a flow rate of 1,000 kg/hr was passed through a first heat exchanger 410 at a temperature of 211° C., mixed with a first stream of a side discharge stream from a decomposition device 300, supplied to a mixing device 100 in a state of being cooled to 80° C. by passing the stream through a cooler 500, and mixed with a process water stream at pH 4 in the mixing device 100. A flow ratio of the phenol-based by-product stream:the first stream of the side discharge stream from the decomposition device 300:the process water stream was controlled to 1:0.25:1.25, based on 1,000 kg/hr of the phenol-based by-product stream.

The discharge stream from the mixing device 100 was supplied to a layer separation device 200 and retained for 5 hours in the layer separation device 200, and an oil stream discharged therefrom was supplied to the decomposition device 300 operated at 0.1 KG in a state of being heated to 190° C. by passing the stream through the first heat exchanger 410 and the second heat exchanger 420.

Effective components were obtained from the upper discharge stream from the decomposition device 300, the first stream of the side discharge stream discharged at 200° C. was supplied to the mixing device 100, and the second stream was mixed with the lower discharge stream and passed through the second heat exchanger 420 to be discharged.

COMPARATIVE EXAMPLE

Comparative Example 1

Referring to the process flow diagram illustrated in FIG. 4, the process was simulated, using an Aspen Plus simulator from Aspen Technology, Inc. Specifically, a phenol-based by-product stream having the composition shown in Table 1 at a temperature of 211° C. was cooled to 80° C. using a cooler 500 at a flow rate of 1,000 kg/hr, and then supplied to a mixing device 100 with a process water stream at pH 4. A flow ratio of the phenol-based by-product stream: the process water stream introduced to the mixing device 100 was controlled to 1:1.25, based on 1,000 kg/hr of the phenol-based by-product stream.

The discharge stream from the mixing device 100 was supplied to a layer separation device 200 and retained for 5 hours in the layer separation device 200, and an oil stream discharged therefrom was supplied to the decomposition device 300 operated at 0.1 KG.

The effective components were obtained from the upper discharge stream from the decomposition device 300, and the lower discharge stream was discharged.

EXPERIMENTAL EXAMPLES

Experimental Example 1

Temperature (° C.) of the oil streams discharged from the layer separation device 200 supplied to the decomposition layer 300 and amounts of energy used (Gcal/hr) in each process of Examples 1 to 3 and Comparative Example 1 are shown in the following Table 3.

TABLE 3

|  |  | Example 1 | Example 2 | Example 3 | Comparative Example 1 |
|---|---|---|---|---|---|
| Temperature of oil stream (° C.) |  | 136 | 159 | 190 | 80 |
| Amount of energy used | Cooler | 0.22 | 0.38 | 0.22 | 0.38 |
|  | Decomposition device | 0.72 | 0.64 | 0.54 | 0.86 |
| (Gcal/hr) | Total | 0.94 | 1.02 | 0.76 | 1.24 |

Referring to Table 3, in Examples 1 to 3 in which the oil stream discharged from the layer separation device 200 was heated using any one or more of the phenol-based by-product and the mixed stream of the second stream of the side discharge stream and the lower discharge stream from the decomposition device 300, it was confirmed that the amount of energy used in the process was decreased. In particular, in Example 3 in which the oil stream discharged from the layer separation device 200 was heated using the phenol-based by-product stream in the first heat exchanger 410 and the oil stream heated in the first heat exchanger 410 was further heated using a mixed stream of the second stream of the side discharge stream and the lower discharge stream in the second heat exchanger 420, it was confirmed that the amount of energy used was decreased the most.

In comparison, in Comparative Example 1 in which the oil stream discharged from the layer separation device 200 was supplied to the decomposition device 300 without separate heating, it was confirmed that the amount of energy used in the process was significantly increased.

The invention claimed is:

1. A method of decomposing phenol-based by-product, the method comprising:
   introducing a phenol-based by-product stream, a first stream of a side discharge stream from a decomposition device, and a process water stream to a mixing device and mixing the streams;
   introducing a discharge stream from the mixing device to a layer separation device to phase-separate the discharge stream into an oil phase and an aqueous phase;
   passing an oil stream discharged from the layer separation device through any one or more of a first heat exchanger and a second heat exchanger and introducing the oil stream to the decomposition device to carry out decomposition; and
   supplying the first stream of the side discharge stream from the decomposition device to the mixing device, forming a mixed stream of a second stream of the side discharge stream from the decomposition device with a lower discharge stream from the decomposition device and discharging the mixed stream, and recovering effective components from an upper discharge stream from the decomposition device.

2. The method of decomposing phenol-based by-product of claim 1, wherein the phenol-based by-product includes any one or more of phenol-based by-product produced in a phenol preparation process and phenol-based by-product produced in a bisphenol A preparation process.

3. The method of decomposing phenol-based by-product of claim 1, wherein the phenol-based by-product includes one or more selected from the group consisting of bisphenol A, phenol, α-methylstyrene, acetophenone, cumylphenol, and an α-methylstyrene dimer.

4. The method of decomposing phenol-based by-product of claim 1, wherein the side discharge stream from the decomposition device includes one or more selected from the group consisting of phenol, acetophenone, α-methylstyrene, and cumene.

5. The method of decomposing phenol-based by-product of claim 1, wherein the side discharge stream from the decomposition device includes 40 wt % or more of acetophenone.

6. The method of decomposing phenol-based by-product of claim 1, wherein an operation pressure of the decomposition device is 0.1 KG to 3 KG.

7. The method of decomposing phenol-based by-product of claim 1, wherein a temperature of the side discharge stream from the decomposition device is 150° C. to 400° C.

8. The method of decomposing phenol-based by-product of claim 1, wherein the phenol-based by-product stream is supplied to the mixing device after heat exchange with the oil stream discharged from the layer separation device in the first heat exchanger.

9. The method of decomposing phenol-based by-product of claim 8, wherein the mixed stream is heat-exchanged with the oil stream, which has been passed through the first heat exchanger, in the second heat exchanger and then is discharged.

10. The method of decomposing phenol-based by-product of claim 1, wherein the effective components include one or more selected from the group consisting of phenol, α-methylstyrene, and cumene.

11. The method of decomposing phenol-based by-product of claim 1, wherein the phenol-based by-product stream is passed through a cooler before being introduced to the layer separation device.

* * * * *